United States Patent [19]

Cier et al.

[11] 3,984,336

[45] Oct. 5, 1976

[54] LUBRICANT COMPOSITIONS

[75] Inventors: Ronald J. Cier, East Windsor; Albert L. Williams, Princeton; Robert F. Bridger, Hopewell, all of N.J.

[73] Assignee: Mobil Oil Corporation, New York, N.Y.

[22] Filed: Nov. 17, 1975

[21] Appl. No.: 632,755

[52] U.S. Cl. ................................ 252/47.5; 252/47
[51] Int. Cl.$^2$ .................. C10M 1/38; C10M 3/32; C10M 5/28; C10M 7/36
[58] Field of Search ......................... 252/47, 47.5

[56] References Cited
UNITED STATES PATENTS

| | | | |
|---|---|---|---|
| 3,175,974 | 3/1965 | Rai et al. ......................... | 252/47 |
| 3,493,599 | 2/1970 | Ahlbrecht ......................... | 252/47 |
| 3,741,897 | 6/1973 | Gansheimer et al. ............... | 252/47.5 |

*Primary Examiner*—Delbert E. Gantz
*Assistant Examiner*—I. Vaughn
*Attorney, Agent, or Firm*—Charles A. Huggett; Howard M. Flournoy

[57] ABSTRACT

Lubricant compositions are provided, containing as antiwear agents, a β-thiopropionitrile having the structure R—S—CH$_2$CH$_2$CN in which R is alkyl, nitriloalkyl, aralkyl, alkaryl, aryl, or benzothiazolyl, mercaptothiadiazolyl, NCCH$_2$CH$_2$—X—(CH$_2$)$_n$ where X is oxygen or sulfur and n is a whole number from 1 to 20. Particularly contemplated are lubricating oils and greases containing the aforementioned antiwear agents.

14 Claims, No Drawings

LUBRICANT COMPOSITIONS

BACKGROUND OF THE INVENTION

1. Field of the Invention

This invention relates to lubricant compositions, and, in one of its aspects, relates more particularly to improved lubricant compositions in the form of lubricating oils and greases, which normally require improvement in antiwear properties.

2. Description of the Prior Art

It is well known that certain types of lubricant compositions, particularly oils of lubricating viscosities and greases, normally exhibit poor antiwear properties during the course of their performance. In this respect, antiwear additives of the prior art have not exhibited satisfactory antiwear properties in conjunction with low corrosivity to steel, bronze, and other metals. Such metals, are further exemplified in a wide variety of industrial lubricant applications including worm gear sets (steel/bronze), table slides (steel/bronze) and hydraulic pumps (steel/brass or silver/bronze).

SUMMARY OF THE INVENTION

It has now been found that improvement in antiwear properties of lubricant compositions, particularly lubricating oils and greases, can be realized by incorporating in these compositions a β-thiopropionitrile having the structure R—S—CH$_2$CH$_2$CN in which R is alkyl, nitriloalkyl, aralkyl, alkaryl, aryl or benzothiazolyl, mercapto-thiadiazolyl, NCCH$_2$CH$_2$—X—(CH$_2$)$_n$ where X is oxygen or sulfur and n is a whole number from 1 to 20. More particularly in a more specific aspect R can comprise n-propyl, n-butyl, n-hexyl, n-dodecyl, 2-butyl, 2-methyl-1-propyl, t-butyl, B-proprionitrilo, NCCH$_2$CH$_2$S(CH$_2$)$_4$—, NCCH$_2$CH$_2$OCH$_2$CH$_2$—, benzyl, phenyl, 3-methylphenyl, 2-benzothiazolyl, or 2-(5-mercapto-1,3,4-thiadiazolyl). Preferably the alkyl, nitriloalkyl, alkaryl and aralkyl groups contain from 1 to 20 carbon atoms.

In general, the present invention, in its preferred applications, contemplates lubricant compositions of the abovedescribed types which contain a small amount sufficient to impart antiwear properties of the aforementioned β-thiopropionitrile additives. Generally, for most applications, the additive is present in an amount from about 0.1 to about 5%, by weight, and preferably in an amount from about 0.1 to about 1%, by weight. The lubricant compositions contemplated in accordance with the present invention may comprise any materials that normally exhibit insufficient antiwear properties. A field of specific applicability is the improvement of liquid hydrocarbon oils boiling within the range from about 75°F to about 1,000°F. Lubricant oils, improved in accordance with the present invention, may be of any suitable lubricating viscosity range from about 45 SSU at 100°F to about 6,000 SSU at 100°F and, preferably, from about 50 to 250 SSU at 210°F. These oils may have viscosity indexes varying from below 0 to about 100 or higher. Viscosity indexes from about 70 to about 95 are preferred. The average molecular weights of these oils may range from about 250 to about 800. In general, the lubricant may comprise any mineral or synthetic oil of lubricating viscosity.

As herein before indicated, the aforementioned β-thiopropionitriles may be incorporated as antiwear agents in grease compositions. Such greases may comprise a combination of a wide variety of lubricating vehicles and thickening or gelling agents. Thus, greases in which the aforementioned antiwear agents are particularly effective, may comprise any of the aforementioned hydrocarbon oils of lubricating viscosity, as the oil vehicle, and may include mineral or synthetic lubricating oils, particularly of the type herein before described. Such oils can also include hydraulic oils, if so desired. When high temperature stability is not a requirement of the finished grease, mineral oils having a viscosity of at least 40 SSU at 150°F, and particularly those falling within the range from about 60 SSU to about 6,000 SSU at 100°F may be employed. The lubricating vehicles of the improved greases of the present invention, containing the above-described B-thiopropionitrile, are combined with a grease-forming quantity of a thickening agent. For this purpose, a wide variety of materials may be employed. These thickening or gelling agents may include any of the conventional mineral salts or soaps which are dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming greases can be used in preparing the aforementioned improved greases in accordance with the present invention.

DESCRIPTION OF SPECIFIC EMBODIMENTS

The following data and examples will serve to illustrate the β-thiopropionitriles of the present invention and their efficacy as lubricant improvers with respect to antiwear properties. It will be understood, however, that it is not intended the invention be limited to the particular antiwear additives as described, and that various modifications thereof can be employed and will be readily apparent to those skilled in the art.

EXAMPLE 1

Preparation of β-n-Propylmercaptopropionitrile
CH$_3$CH$_2$CH$_2$—S—CH$_2$CH$_2$CN 1-Propanethiol (20.0 g; 0.26 moles) was mixed with sodium methoxide catalyst (0.5 g) and the mixture cooled to below room temperature. Acrylonitrile (13.8 g; 0.26 moles) was added dropwise, the temperature of the reaction mix being kept below 40°C by cooling in an icebath. When the addition of the acrylonitrile was complete the mixture was permitted to come to room temperature and mixing continued for 2 hours. The catalyst was removed by diluting the reaction mixture with diethylether and extracting with dilute hydrochloric acid. The ether solution was then placed on a rotary evaporator and the solvent removed with heat (hot water) and vacuum.

The following spectral properties confirm the structure shown above:

ir(CHCl$_3$) 4.45μ (C ≡ N), 7.02μ (CH$_2$—S—C); nmr(CDCl$_3$) δ1.0(triplet, 2.9 H, CH$_3$), δ1.6 (multiplet, 2.0 H, CH$_2$ alpha to CH$_3$), δ2.5–2.8 (multiplet containing 2 overlapping triplets, 6.1 H, 2-CH$_2$ alpha to S and 1-CH$_2$ alpha to C ≡ N).

Analysis: Calc. for C$_6$H$_{11}$NS: C, 55.77%; H, 8.58%; N, 10.84%; S, 24.81%. Found: C, 55.72%; H, 8.60%; N, 10.90%; S, 24.81%.

EXAMPLE 2

Preparation of β-n-Butylmercaptopropionitrile
CH$_3$CH$_2$CH$_2$CH$_2$—S—CH$_2$CH$_2$CN β-n-Butylmercaptopropionitrile was prepared according to the procedure of Example 1 using 1-butanethiol (20.0 g; 0.22 moles), acrylonitrile (11.7 g; 0.22 moles) and sodium methoxide (0.5 g).

The following spectral properties confirm the structure shown above:

ir(CHCl$_3$) 4.45μ (C ≡ N), 7.04μ (CH$_2$—S—C); nmr (CDCl$_3$) δ0.9 (triplet, 2.9 H, CH$_3$), δ1.5 (envelope, 4.2 H, 2-CH$_2$ in alkyl), δ2.5–2.75 (multiplet containing 2 overlapping triplets, 5.9 H, 2-CH$_2$ alpha to S and 1-CH$_2$ alpha to C ≡ N).

Analysis: Calc. for C$_7$H$_{13}$NS: C, 58.69%; H, 9.15%; N, 9.78%; S, 22.38%. Found: C, 58.08%; H, 9.32%; N, 10.1%; S, 20.6%.

EXAMPLE 3

Preparation of β-n-Hexylmercaptopropionitrile
CH$_3$(CH$_2$)$_5$—S—CH$_2$CH$_2$CN β-n-Hexylmercaptopropionitrile was prepared according to the procedure of Example 1 using 1-hexanethiol (25.0 g; 0.21 moles), acrylonitrile (11.2 g; 0.21 moles) and sodium methoxide (0.5 g).

The following spectral properties confirm the structure shown above:

ir(CHCl$_3$) 4.45μ (C ≡ N), 7.03 μ (CH$_2$—S—C); nmr (CDCl$_3$) δ0.9 (triplet, 3.0 H, CH$_3$), ca δ1.5 (broad singlet, 8.1 H, 4-CH$_2$ in alkyl), δ2.5–2.8 (multiplet, 5.9 H, 2-CH$_2$ alpha to S and 1-CH$_2$ alpha to C ≡ N)

Analysis: Calc. for C$_9$H$_{17}$NS: C, 63.10%; H, 10.00%; N, 8.18%; S, 18.72%. Found: C, 63.05%; H, 10.05%; N, 8.29%; S, 18.72%.

EXAMPLE 4

Preparation of β-n-Dodecylmercaptopropionitrile
CH$_3$(CH$_2$)$_{11}$—S—CH$_2$CH$_2$CN β-n-Dodecylmercaptopropionitrile was prepared according to the procedure of Example 1 using 1-dodecanethiol (24.75 g; 0.12 moles), acrylonitrile (6.4 g; 0.21 moles) and sodium methoxide (0.5 g).

The following spectral properties confirm the structure shown above:

ir(CHCl$_3$) 4.45μ (C ≡ N), 7.05μ (CH$_2$—S—C); nmr (CDCl$_3$) δ1.1 (broad singlet with triplet shoulder, 23.3 H, n-C$_{11}$H$_{23}$), δ2.5–2.75 (multiplet, 5.7 H, 2-CH$_2$ alpha to S and 1-CH$_2$ alpha to C ≡ N)

Analysis: Calc. for C$_{15}$H$_{29}$NS: C, 70.52%; H, 11.44%; N, 5.48%; S, 12.55%. Found: C, 70.68%; H, 11.31%; N, 5.95%; S, 11.4%.

EXAMPLE 5

Preparation of
β-(1-Methyl-1-propylmercapto)propionitrile

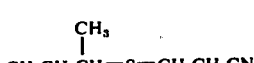

β-(1-Methyl-1-propylmercapto)propionitrile was prepared according to the procedure of Example 1 using 1-methyl-1-propanethiol (25.0 g; 0.28 moles), acrylonitrile (14.9 g; 0.28 moles) and sodium methoxide (0.5 g).

The following spectral properties confirm the structure shown above:

ir(CHCl$_3$) 4.43μ (C ≡ N), 7.01μ (CH$_2$—S—C); nmr (CDCl$_3$) δ0.9–1.7 (multiplet; 7.8μ, 2-CH$_3$ and 1-CH$_2$ alpha to CH$_3$), δ2.4–3.0 (multiplet, 5.2 H, 1-CH alpha to S, 1-CH$_2$ alpha to S and 1-CH$_2$ alpha to C ≡ N).

Analysis: Calc. for C$_7$H$_{13}$NS: C, 58.69%; H, 9.15%; N, 9.78%; S, 22.38%. Found: C, 58.82%; H, 8.92%; N, 10.3%; S, 19.8%.

EXAMPLE 6

Preparation of
β-(2-Methyl-1-propylmercapto)propionitrile

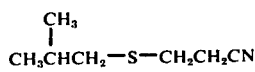

β-(2-Methyl-1-propylmercapto)propionitrile was prepared according to the procedure of Example 1 using 2-methyl-1-propanethiol (25.0 g; 0.28 moles), acrylonitrile (14.9 g; 0.28 moles) and sodium methoxide (0.5 g).

The following spectral properties confirm the structure shown above:

ir(CHCl$_3$) 4.43μ (C ≡ N), 7.03μ (CH$_2$—S—C); nmr (CDCl$_3$) δ1.0 (doublet, 5.7 H, 2-CH$_3$ alpha to CH), δ1.8 (multiplet, 1.3 H, CH), δ2.4–2.75 (multiplet, 6.0 H, 2-CH$_2$ alpha to S and 1-CH$_2$ alpha to C ≡ N).

Analysis: Calc. for C$_7$H$_{13}$NS: C, 58.69%; H, 9.15%; N, 9.78%; S, 22.38%. Found: C, 58.65%; H, 9.03%; N, 10.6%; S, 19.5%.

EXAMPLE 7

Preparation of
β-(2-Methyl-2-propylmercapto)propionitrile

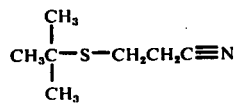

β-(2-Methyl-2-propylmercapto)propionitrile was prepared according to the procedure of Example 1 using 2-methyl-2-propanethiol according to the procedure of Example 1 using 2-methyl-2-propanethiol (25.0 g; 0.28 moles), acrylonitrile (14.9 g; 0.28 moles) and sodium methoxide (0.5 g).

The following spectral properties confirm the structure shown above:

ir(CHCl$_3$) 4.43μ (C ≡ N), 7.02μ (CH$_2$—S—C); nmr (CDCl$_3$) δ1.3 (sharp singlet, 8.9 H, 3-CH$_3$ on tertiary C); δ2.6–2.8 (2 overlapping triplets, 4.1 H, S—CH$_2$CH$_2$—C ≡ N)

Analysis: Calc. for C$_7$H$_{13}$NS: C, 58.69%; H, 9.15%; N, 9.78%; S, 22.38%. Found: C, 60.04%; H, 9.15%; N, 10.6%; S, 19.0%.

EXAMPLE 8

Preparation of β,β'-Thiodipropionitrile
NCCH₂CH₂—S—CH₂CH₂CN

β,β'-Thiodipropionitrile is a known compound and can be prepared as described in U.S. Pat. No. 2,790,821. For the present purposes, β,β'-Thiodipropionitrile was prepared in the following manner:

Primene JMT (33.0 g; 0.1 moles), a primary amine having a molecular weight of approximately 330, was added dropwise to a mixture containing carbon disulfide (8.4 g; 0.11 moles) and acrylonitrile (10.6 g; 0.2 moles). When the addition was complete the mixture was heated to 100° C for 18 hours. The reaction mixture, which was now comprised of 2 immiscible layers, was allowed to cool and the lower comprised of 2 immiscible layers, was allowed to cool and the lower layer (β,β'-Thiodipropionitrile) separated from the mixture.

The following spectral properties confirm the structure shown above:

ir(CHCl₃) 4.43μ (C ≡ N), 7.02μ (CH₂—S—C); nmr (CDCl₃) δ2.5-3.0 (multiplet, S—CH₂CH₂—C ≡ N)

Analysis: Calc. for C₆H₈N₂S: C, 51.40%; H, 5.75%; N, 19.98%; S, 22.87%. Found: C, 51.27%; H, 5.90%; N, 19.74%; S, 23.07%.

EXAMPLE 9

Preparation of 4,9-Dithiadodecanedinitrile
NCCH₂CH₂—S—CH₂CH₂CH₂CH₂—S—CH₂CH₂CN 4,9-Dithiadodecanedinitrile was prepared according to the procedure of Example 1 using 1,4-butanedithiol (20.0 g; 0.16 moles), acrylonitrile (17.0 g; 0.32 moles) and benzyltrimethylammonium hydroxide (40% in methanol; 1 ml) as the catalyst.

The following spectral properties confirm the structure shown above:

ir (neat) 4.45μ (C ≡ N), 7.04μ (CH₂—S—C); nmr (Acetone-d₆) δ1.7 (multiplet, 3.6 H, 2-CH₂ in C₄ chain beta to S), δ2.5-3.0 (multiplet, 12.3 H, 4-CH₂ alpha to S and 2-CH₂ alpha to C ≡ N).

Analysis: Calc. for C₁₀H₁₆N₂S₂: C, 52.59%; H, 7.06%; N, 12.27%; S, 28.08%. Found: C, 52.59%; H, 7.06%; N, 12.27%; S, 23.63%.

4,9-Dithiadodecanedinitrile is believed to be a new compound.

EXAMPLE 10

Preparation of 4-Oxa-7-thiadecanedinitrile
NCCH₂CH₂—O—CH₂CH₂—S—CH₂CH₂CN

4-Oxa-7-thiadecanedinitrile was prepared according to the procedure of Example 1 using 2-mercaptoethanol (25.0 g; 0.32 moles), acrylonitrile (34.0 g; 0.64 moles) and benzyltrimethylammonium hydroxide (40% in methanol; 1 ml) as the catalyst.

The following spectral properties confirm the structure shown above:

ir(CHCl₃) 4.44μ (C ≡ N), 7.04μ (CH₂—S—C), 8.95μ (CH₂—O—CH₂); nmr (CDCl₃) δ2.2-3.1 (multiplet, 8.0 H, 2-CH₂ alpha to S and 2-CH₂ alpha to C ≡ N), δ3.6-3.8 (multiplet containing 2 overlapping triplets, 4.0 H, CH₂—O—CH₂)

Analysis: Calc. for C₈H₁₂N₂OS: C, 52.15%; H, 6.56%; N, 15.20%; O, 8.68%; S, 17.40%. Found: C, 50.56%; H, 7.09%; N, 15.3%; S, 17.5%.

EXAMPLE 11

Preparation of β-Benzylmercaptopropionitrile

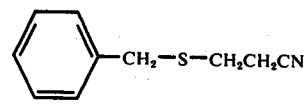

β-Benzylmercaptopropionitrile was prepared according to the procedure of Example 1 using α-toluenethiol (25.0 g; 0.20 moles), acrylonitrile (10.6 g; 0.20 moles) and sodium methoxide (0.5 g).

The following spectral properties confirm the structure shown above:

ir(CHCl₃) 4.43μ (C ≡ N), 7.02μ (CH₂—S—C); nmr (CDCl₃) δ2.5 (2 overlapping triplets, 4.0 H, S—CH₂C-H₂—C ≡ N), δ3.7 (sharp singlet, 1.9 H, benzyl CH₂), δ7.3 (sharp singlet, 5.1 H, aromatic ring).

Analysis: Calc. for C₁₀H₁₁NS: C, 67.76%; H, 6.26%; N, 7.90%; S, 18.09%. Found: C, 67.38%; H, 6.23%; N, 7.78%; S, 18.59%.

EXAMPLE 12

Preparation of β-Phenylmercaptopropionitrile

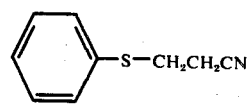

β-Phenylmercaptopropionitrile was prepared according to the procedure of Example 1 using thiophenol (25.0 g; 0.23 moles), acrylonitrile (12.2 g; 0.23 moles) and sodium methoxide (0.5 g).

The following spectral properties confirm the structure shown above:

ir(CHCl₃) 4.44μ (C ≡ N), 7.02μ (CH₂—S—C); nmr (CDCl₃) δ2.5 (triplet, 2.1 H, CH₂ alpha to C ≡ N), δ3.1 (triplet, 2.1 H, CH₂ alpha to S), δ7.3 (multiplet, 5.0 H, aromatic ring).

Analysis: Calc. for C₉H₉NS: C, 66.22%; H, 5.56%; N, 8.58%; S, 19.64%. Found: C, 65.64%; H, 5.81%; N, 9.47%; S, 18.97%.

EXAMPLE 13

Preparation of β-(3-Methylphenyl)mercaptopropionitrile

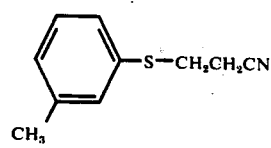

β-(3-Methylphenyl)mercaptopropionitrile was prepared according to the procedure of Example 1 using m-toluenethiol (20.0 g; 0.16 moles), acrylonitrile (8.6 g; 0.16 moles) and sodium methoxide (0.5 g).

The following spectral properties confirm the structure shown above:

ir(CHCl₃) 4.43μ (C ≡ N), 7.02μ (CH₂—S—C); nmr (CDCl₃) δ2.3-2.5 (multiplet composed of overlapping singlet and triplet, 5.0 H, CH₃ on ring and CH₂ alpha to C≡N), δ3.0 (triplet, 2.0 H, CH₂ alpha to S), δ7.1 (multiplet, 4.0 H, aromatic ring)

Analysis: Calc. for C₁₀H₁₁NS: C, 67.76%; H, 6.26%; N, 7.90%; S, 18.09%. Found: C, 67.41%; H, 6.29%; N, 7.76%; S, 18.43%.

EXAMPLE 14

Preparation of β-(2-Benzothiazolyl)mercaptopropionitrile

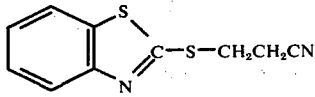

2-Mercaptobenzothiazole (25.0 g; 0.15 moles) was mixed with t-butanol (125 ml) and benzyltrimethylammonium hydroxide (40% in methanol; 3 ml). Acrylonitrile (15.9 g; 0.30 moles) was added dropwise and the mixture stirred at room temperature for 7 days. The product was removed by filtration and recrystallized from benzene.

The following spectral properties confirm the structure shown above:

ir(CHCl₃) 4.44μ (C≡N), 7.27μ (CH₂—S—C); nmr (CDCl₃) δ3.0 (triplet, 2.0 H, CH₂ alpha to C≡N), δ4.7 (triplet, 2.0 H, CH₂ alpha to S), δ7.5 (multiplet, 3.9 H, aromatic ring).

Analysis: Calc. for C₁₀H₈N₂S₂: C, 54.51%; H, 3.66%; N, 12.72%; S, 29.10%. Found: C, 54.51%; H, 3.48%; N, 12.52%; S, 29.10%.

EXAMPLE 15

Preparation of β-[2-(5-Mercapto-1,3,4-thiadiazolyl)]-mercaptopropionitrile

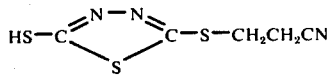

β-[2-(5-Mercapto-1,3,4-thiadiazolyl)]mercaptopropionitrile was prepared according to the procedure of Example 14 using 2,5-dimercapto-1,3,4-thiadiazole (25.0 g; 0.17 moles), acrylonitrile (30.8 g; 0.58 moles), benzyltrimethylammonium hydroxide (40% in methanol; 1 ml) and t-butanol (75 ml).

The following spectral properties confirm the structure shown above:

ir(KBr) 4.43μ (C≡N); nmr (Acetone-d₆) δ3.0 (triplet, 2.0 H, CH₂ alpha to C≡N), δ3.5 (triplet, 2.0 H, CH₂ alpha to S)

Analysis: Calc. for C₅H₅N₃S₃: C, 29.54%; H, 2.48%; N, 20.67%; S, 47.31%. Found: C, 29.67%; H, 2.02%; N, 20.71%; S, 47.64%.

β-[2-(5-Mercapto-1,3,4-thiadiazolyl)]mercaptopropionitrile is believed to be a new compound.

Testing Method

Additives were tested for antiwear activity using the four Ball Wear Test, disclosed in U.S. Pat. No. 3,423,316. In general, in this test three steel balls of SAE 52100 steel are held in a ball cup. A fourth ball positioned on a rotatable vertical axis is brought into contact with the three balls and is rotated against them. The force with which the fourth is held against the three stationary balls may be varied according to a desired load. The test lubricant is added to the ball cup and acts as a lubricant for the rotation. At the end of the test, the steel balls are investigated for wear scar. The extent of scarring represents the effectiveness of the lubricant as an antiwear agent. Results are also reported as wear rates in volume of wear per unit sliding distance per kilogram load. The lower the wear rate, the more effective the lubricant as an antiwear agent. The base stock oil employed in accordance with the test results shown in Table 1 comprised a 150 SSU at 210° F solvent-refined paraffinic bright stock lubricating oil. In the data summarized in Table 1, all additives were tested at equimolar concentrations of 0.2 moles per kilogram of oil; the corresponding weight percentages are shown in the table. Standard conditions of 40 kg load, 600 rpm, and 30 minutes' test time were employed at 200° F.

TABLE 1

FOUR BALL WEAR TEST RESULTS
40 Kg load, 600 rpm, 30 minutes

| Example | Compounds | Wt. % | 200°F Coefficient of Friction | Wear Scar Diameter mm | Wear Rate × 10⁻¹² cc/cm-kg |
|---|---|---|---|---|---|
|  | Base Stock Only | — | 0.087 | 0.686 | 4.60 |
| 1 | CH₃CH₂CH₂—S—CH₂CH₂CN | 0.26 | .091 | 0.424 | .48 |
| 2 | CH₃CH₂CH₂CH₂—S—CH₂CH₂CN | 0.29 | 0.072 | 0.445 | 0.62 |
| 3 | CH₃(CH₂)₅—SCH₂CH₂CN | 0.34 | 0.085 | 0.445 | 0.62 |
| 4 | CH₃(CH₂)₁₁—SCH₂CH₂CN | 0.51 | 0.090 | 0.516 | 1.29 |
| 5 | CH₃CH₂CH(CH₃)—SCH₂CH₂CN | 0.29 | .078 | 0.432 | 0.53 |
| 6 | (CH₃)₂CHCH₂SCH₂CH₂CN | 0.29 | 0.088 | 0.470 | 0.82 |
| 7 | (CH₃)₃C—S—CH₂CH₂CN | 0.29 | 0.075 | 0.385 | 0.27 |
| 8 | (N≡C—CH₂CH₂)₂S | 0.28 | 0.068 | 0.335 | 0.08 |
| 9 | NCCH₂CH₂S(CH₂)₄SCH₂CH₂CN | 0.46 | 0.065 | 0.356 | .15 |
| 10 | NCCH₂CH₂OCH₂CH₂SCH₂CH₂CN | 0.37 | 0.059 | 0.356 | .15 |
|  | Base Stock Only | — | 0.087 | 0.686 | 4.60 |
| 11 | C₆H₅—CH₂—S—CH₂CH₂CN | 0.35 | 0.076 | 0.373 | 0.21 |

TABLE 1-continued

FOUR BALL WEAR TEST RESULTS
40 Kg load, 600 rpm, 30 minutes

| Example | Compounds | Wt. % | Coefficient of Friction | Wear Scar Diameter mm (200°F) | Wear Rate × 10⁻¹² cc/cm-kg |
|---|---|---|---|---|---|
| 12 | 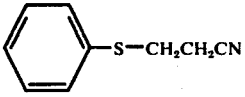 | 0.33 | 0.085 | 0.437 | 0.56 |
| 13 | 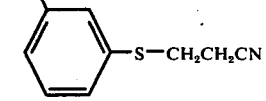 | 0.35 | 0.085 | 0.406 | 0.37 |
| 14 | 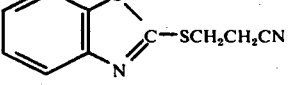 | 0.44 | .085 | 0.363 | 0.18 |
| 15 | 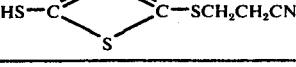 | 0.41 | .082 | 0.483 | 0.94 |

As will be apparent from the data of the foregoing Table 1, the lubricant compositions of the present invention exhibit highly improved antiwear properties, as evidenced by the indicated comparative data with respect to wear scar diameter and wear rate.

While the present invention has been described with reference to preferred compositions and modifications thereof, it will be apparent to those skilled in the art that departure from the preferred embodiments can be effectively made and are within the scope of the specification.

We claim:

1. A lubricant composition containing an antiwear amount of a β-thiopriopionitrile having the structure R—S—CH₂CH₂CN in which R is alkyl, nitriloalkyl, aralkyl, alkaryl, aryl or benzothiazolyl, mercaptothiadiazolyl, NCCH₂CH₂—X—(CH₂)ₙ where X is oxygen or sulfur and n is a whole number from 1 to 20.

2. The lubricant composition defined in claim 1 wherein the alkyl, nitriloalkyl, alkaryl and aralkyl groups contain from 1 to 20 carbon atoms.

3. The lubricant composition defined in claim 1 wherein R is n-propyl, n-butyl, n-hexyl, n-dodecyl, 2-butyl, 2-methyl-1-propyl, t-butyl, B-propionitrilo, NCCH₂CH₂S(CH₂)₄—, NCCH₂CH₂OCH₂CH₂—, benzyl, phenyl, 3-methylphenyl, 2-benzothiazolyl, or 2-(5-mercapto-1,3,4-thiadiazolyl).

4. The lubricant composition defined in claim 1 wherein the β-thiopropionitrile is β-n-butylmercaptopropionitrile.

5. The lubricant composition defined in claim 1 wherein the β-thiopropionitrile is β-[2-(5-mercapto-1,3,4-thiadiazolyl)]-mercaptopropionitrile.

6. The lubricant composition defined in claim 1 wherein the β-thiopropionitrile is β,β'-thiodipropionitrile.

7. The lubricant composition defined in claim 1 wherein the β-thiopropionitrile is 4-Oxa-7-thiadecanedinitrile.

8. The lubricant composition defined in claim 1 wherein the β-thiopropionitrile is β-(2-benzothiazolyl)-mercaptopropionitrile.

9. The lubricant composition defined in claim 1 wherein the β-thiopropionitrile is present in an amount from about 0.1 to about 5%, by weight.

10. The lubricant composition defined in claim 1 wherein the β-thiopropionitrile is present in an amount from about 0.1 to about 1%, by weight.

11. The lubricant composition defined in claim 1 wherein said lubricant comprises an oil of lubricating viscosity.

12. The lubricant composition defined in claim 1 wherein said lubricant comprises a mineral oil.

13. The lubricant composition defined in claim 1 wherein said lubricant comprises a synthetic oil.

14. The lubricant composition defined in claim 1 wherein said lubricant comprises a grease.

* * * * *